(12) United States Patent
Pitkanen et al.

(10) Patent No.: US 7,632,673 B2
(45) Date of Patent: Dec. 15, 2009

(54) REACTOR DEVICE

(75) Inventors: Juha-Pekka Pitkanen, Helsinki (FI); Antii Vuolanto, Kirkkonummi (FI)

(73) Assignee: Medicel Oy, Helsinki (FI)

( * ) Notice: Subject to any disclaimer, the term of this patent is extended or adjusted under 35 U.S.C. 154(b) by 399 days.

(21) Appl. No.: 11/261,604

(22) Filed: Oct. 31, 2005

(65) Prior Publication Data
US 2006/0105448 A1 May 18, 2006

(30) Foreign Application Priority Data
Nov. 3, 2004 (FI) ................................. 20045416

(51) Int. Cl.
C12M 1/34 (2006.01)
C12M 3/00 (2006.01)
(52) U.S. Cl. .............. 435/287.1; 435/286.5; 435/289.1; 435/813; 435/819
(58) Field of Classification Search .............. 435/286.5, 435/309.1, 162, 307, 813, 819
See application file for complete search history.

(56) References Cited
U.S. PATENT DOCUMENTS 3,847,749 A * 11/1974 Smith et al. .............. 435/286.5
4,269,212 A 5/1981 Kaartinen
4,650,766 A * 3/1987 Harm et al. ............... 435/286.6
4,696,902 A 9/1987 Bisconte
5,961,925 A * 10/1999 Ruediger et al. .............. 422/99
6,635,441 B2 10/2003 Downs et al.
6,803,238 B1 10/2004 Eggers
2002/0137197 A1* 9/2002 Ammann et al. ......... 435/287.2
2004/0082055 A1* 4/2004 Hince et al. .............. 435/262.5
2004/0115829 A1 6/2004 Kaartinen et al.
2005/0112549 A1* 5/2005 Baumgardner et al. ......... 435/4

FOREIGN PATENT DOCUMENTS

GB 1 408 306 10/1975
GB 1 417 560 12/1975
WO WO 03/093406 A2 11/2003

* cited by examiner

Primary Examiner—William H Beisner
Assistant Examiner—Michael Hobbs
(74) Attorney, Agent, or Firm—Barnes & Thornburg LLP

(57) ABSTRACT

The invention relates to a reactor device. In order to keep the equipment costs low and to make it possible to handle a plurality of cultivations during a short time period, the device includes a channel and mechanism for delivering fluid to a monitor; reactor vessels for containing fluid, connected to the channel via valves; a source for a cleaning fluid, connected to the channel via a valve; and a controller for controlling the mechanism for delivering fluid, the monitor and the valves for taking samples from selected reactor vessels one by one, for delivering the samples to the monitoring mechanism, and for cleaning the channel by delivering cleaning fluid through the channel.

8 Claims, 6 Drawing Sheets

REACTOR DEVICE

This non-provisional application relies for priority upon Finnish Patent Application No. 20045416, filed Nov. 3, 2004, the contents of which are incorporated herein by reference in their entirety.

BACKGROUND OF THE INVENTION

1. Field of the Invention

This invention relates to a reactor device which can be used for culturing cells, such as bacteria, yeast and fungi. In the following the invention will be described, by way of example, by referring mainly to microbial cultivation. It should, however, be observed that the reactor device can also be used for other purposes, such as tissue culture, biotransformations or chemical reactions.

2. Description of Prior Art

There are known bioreactors equipped with the necessary equipment in order to produce and control the environment needed for cultivation. However, the cultivation of microorganisms in existing bioreactors is time-consuming and laborious. The existing bioreactor equipment contains only one reactor vessel containing automated monitoring and control loops to control, for example, cultivation temperature, agitation and pH-value. Also other instruments, such as for monitoring dissolved oxygen or optical density, can be added.

The most serious drawback with the above described prior art solution is the costs involved. The price of the equipment and also the costs caused by the labor needed for manually operating the bioreactor and taking the samples are high, sometimes requiring overnight sampling. Additionally, for screening and optimization purposes a high number of cultivations are needed. In the existing bioreactors the equipment can be used only for one cultivation at a time. Thus, the time needed for experiments involving a large number of cultivations is naturally very long.

SUMMARY OF THE INVENTION

The object of the present invention is to solve the above mentioned problems and to provide a reactor device which makes it possible to carry out experiments involving a large number of cultivations in a more efficient and economical way. This and other objects of the invention are achieved with the reactor device of independent claim 1.

The reactor device of the present invention comprises a plurality of reactor vessels. Thus the reactor device can be used simultaneously for several cultivations. The monitoring means of the reactor device, in other words the equipment which makes it possible to process the samples in such a way that the progress in the reactor vessels can be monitored, can automatically be used for all the samples. Thus, the equipment costs for a single cultivation will be significantly reduced and the time needed for experiments involving a large number of cultivations is also significantly reduced. Also the amount of manual work needed for a single cultivation can be significantly reduced, as the reactor device offers the possibility to automatically take samples from the reactor vessels and to feed these samples one by one to the monitoring means.

The monitoring means may consist only of a storage for storing separately the samples taken from the different reactor vessel. In this case the analyzing of the sample in order to monitor the progress in the corresponding reactor vessel is done later on, for instance, manually. Alternatively the monitoring means may include an in-line device which automatically measures the critical parameters of the samples.

The preferred embodiments of the reactor device are disclosed in dependent claims 2-9.

BRIEF DESCRIPTION OF DRAWINGS

In the following the invention will be described in closer detail by way of example and with reference to the attached drawings, in which.

DESCRIPTION OF PREFERRED EMBODIMENTS

Figure 1:
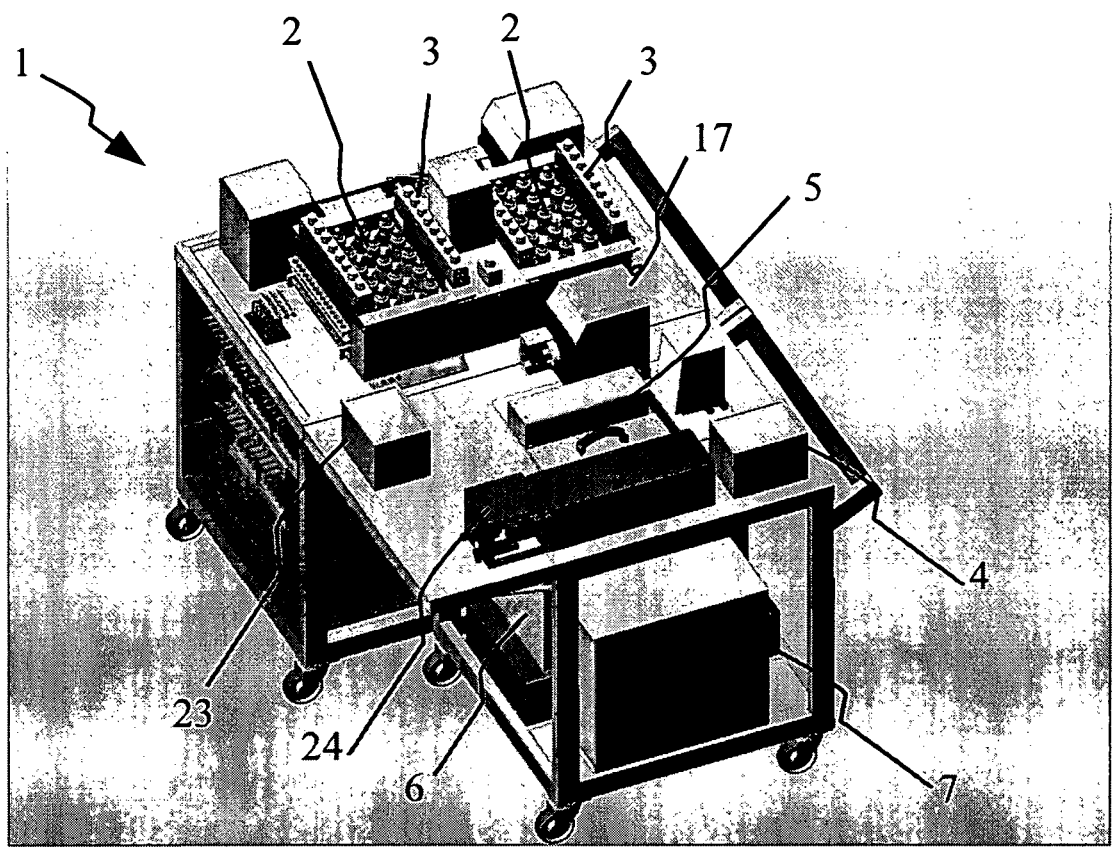
FIG. 1 shows a first preferred embodiment of a reactor device according to the invention.

FIG. 1 shows a first preferred embodiment of a reactor device 1 according to the invention. In the following example it is assumed that the reactor device shown in the figures is used to handle and monitor microbial cultivations. For this purpose the reactor device 1 includes a plurality of reactor vessels 2 which are connected to a channel via valves 3.

The reactor device includes, according to the present invention, a monitoring means which makes it possible to process the samples in such a way that the progress in the reactor vessels can be monitored. In the figures it is assumed, by way of example, that the reactor device includes both an in-line device 4, which makes it possible to automatically obtain immediate measurement results from the samples, and a storage means 5, where the samples can be separately stored for later analyzing, in which case the results of the analysis make it possible to monitor the progress in the reactor vessels. In practice it is, however, sufficient to have either one of these apparatus included in the monitoring means.

In FIG. 1 a pump 17 is attached to the channel for delivering fluid from the channel to the in-line device 4. The in-line device 4 may consist, for instance, of a device for measuring pH of a sample, a device for measuring DO (Dissolved Oxygen) of a sample, an in-line microscope with a camera for capturing a picture of a sample, or a combination of these.

In the embodiment shown in the figures the reactor device is also equipped with a storage means 5 where a plurality of containers can be arranged such that each sample taken from one of the reactor vessels 2 is fed into a separate container. This makes it possible to store the samples for later analyzing, in order to monitor the progress in the reactor vessels based on the results of the analyzing. In case the reactor device 1 is equipped with a storage device, then the containers of the storage device are preferably arranged in a cold chamber 6. The temperature of the cold chamber can be around −40° C., for instance, in order to stop or slow down the chemical reactions occurring in the samples as fast as possible. In addition and for the same purpose, the containers of the storage means 5 can contain cold (−40° C.) 60%-methanol, into which the samples are sprayed.

The reactor device 1 also includes a controller 7, which may consist of a programmable apparatus, such as an ordinary PC (Personal Computer). The controller controls the operation of the valves 3, the pump 17, and the monitoring means (in-line device 4 and storage means 5), as will be apparent from the following explanations.

In FIG. 1 the reactor device 1 further comprises a device 23 for delivering a chemical modification to the sample, and a device 24 for controlling the contact time between a chemical modification fluid and the sample. These devices, which are not absolutely necessary in order to carry out the invention, are described in closer detail in connection with FIGS. 6 and 7.

Figure 2:
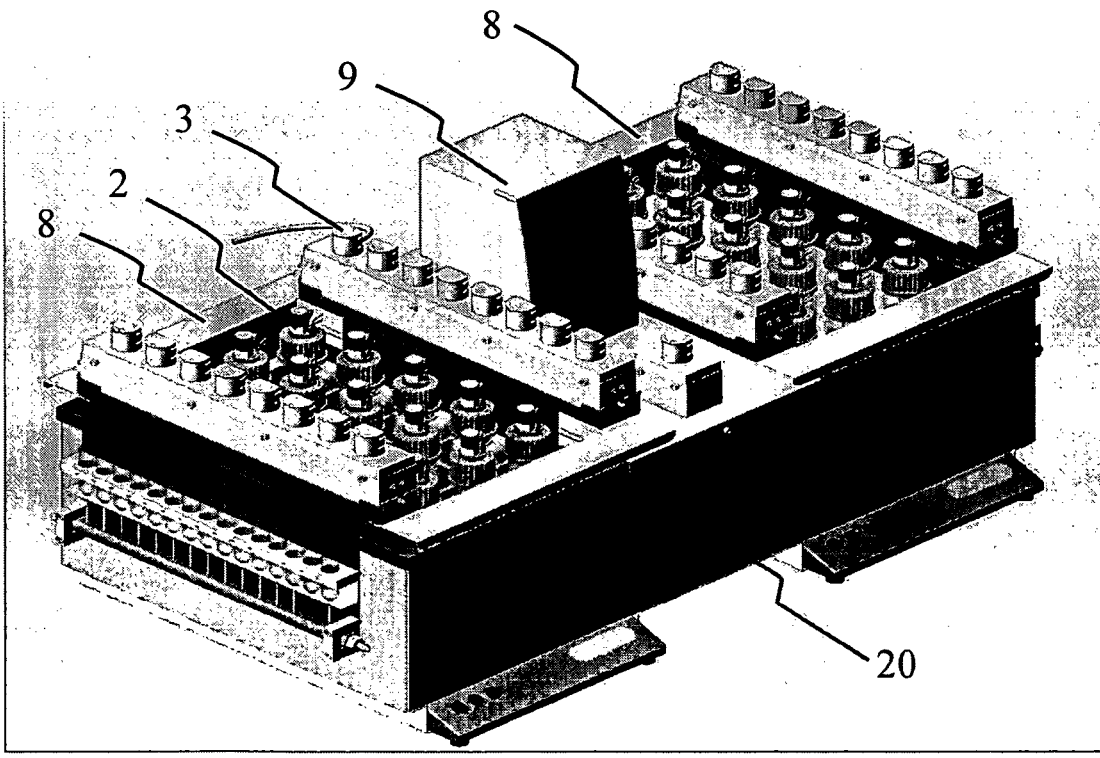
FIGS. 2 and 3 show details of a reactor vessel stand for the device shown in FIG. 1.
Figure 3:
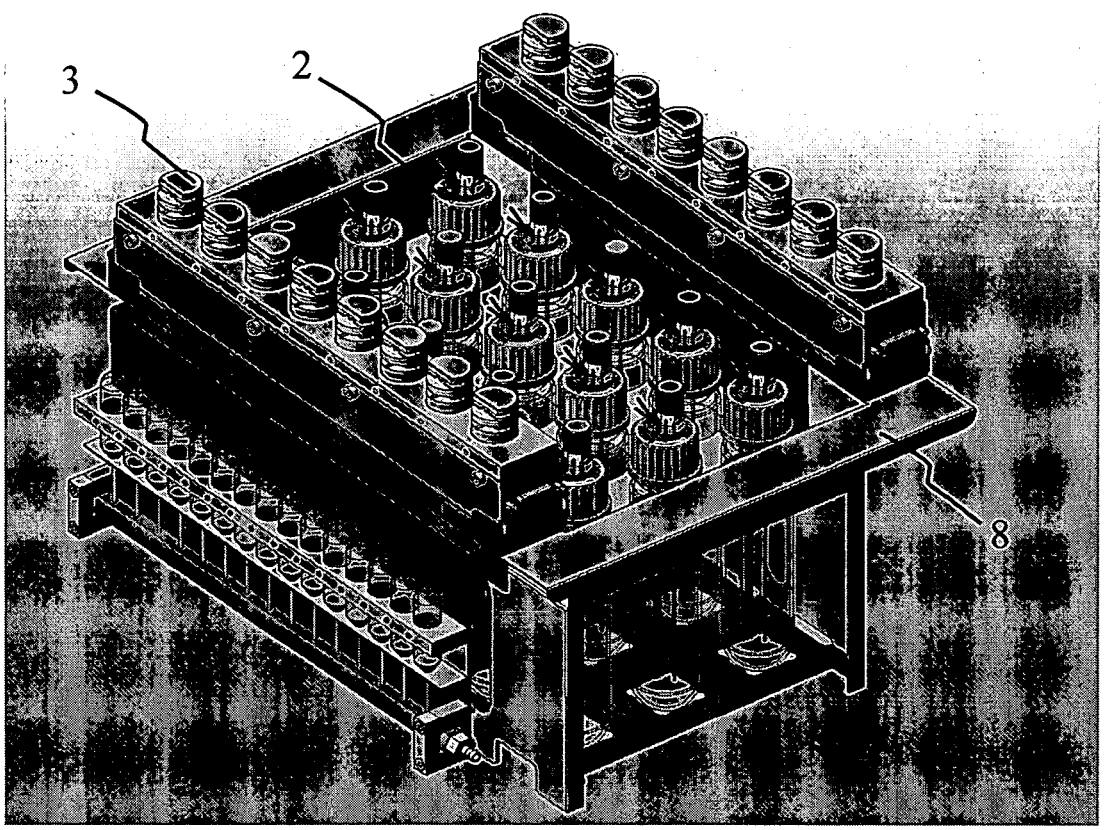

FIGS. 2 and 3 show details of a reactor vessel stand for the device shown in FIG. 1. The reactor vessels 2 have been arranged in predetermined positions in a stand 8. In FIG. 2 two stands 8 are shown. The stands 8 are arranged into a fluid bath 20 such that the reactor vessels 2 are at least partly surrounded by the fluid (for instance water) in the fluid bath 20. The reactor vessel comprises means 9 for adjusting the temperature of the fluid bath in order to keep the temperature within a predetermined range suitable for the cultivation.

Figure 4:
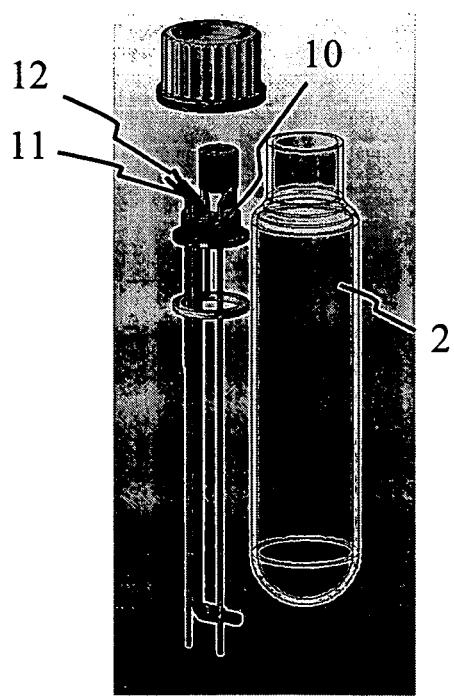
FIG. 4 shows a reactor vessel.

FIG. 4 shows a reactor vessel 2. The reactor vessel 2 can be made of glass, for instance, and it can be provided with a metal lid 10 on which an outlet 11 is mounted. According to the invention, it is sufficient to have only an outlet 11 which can be connected to the channel in order to obtain a sample from the reactor vessel 2 for monitoring purposes. However, it is possible to have also additional inlets/outlets in the reactor vessel.

One alternative is to provide the reactor vessel 2 with an inlet 12 for fluid, which makes it possible to accomplish continuous operation by introducing fluid into the reactor vessel 2 during operation. In addition other inlets/outlets can be arranged in the reactor vessel, such as an air/gas inlet for aeration or other gas dosage, a septum lead-in for manual manipulation (in or out), a waste outlet for gas and liquid phase waste, and an extra inlet/outlet connection to be used when needed. The reactor vessel 2 can further be equipped with a magnetic stirring system providing adequate mixing and/or with a sinter connected to the gas inlet in order to produce small, uniform gas bubbles and to improve uniform mixing. The reactor vessel and the lid can be sterilized by autoclaving.

Figure 5:
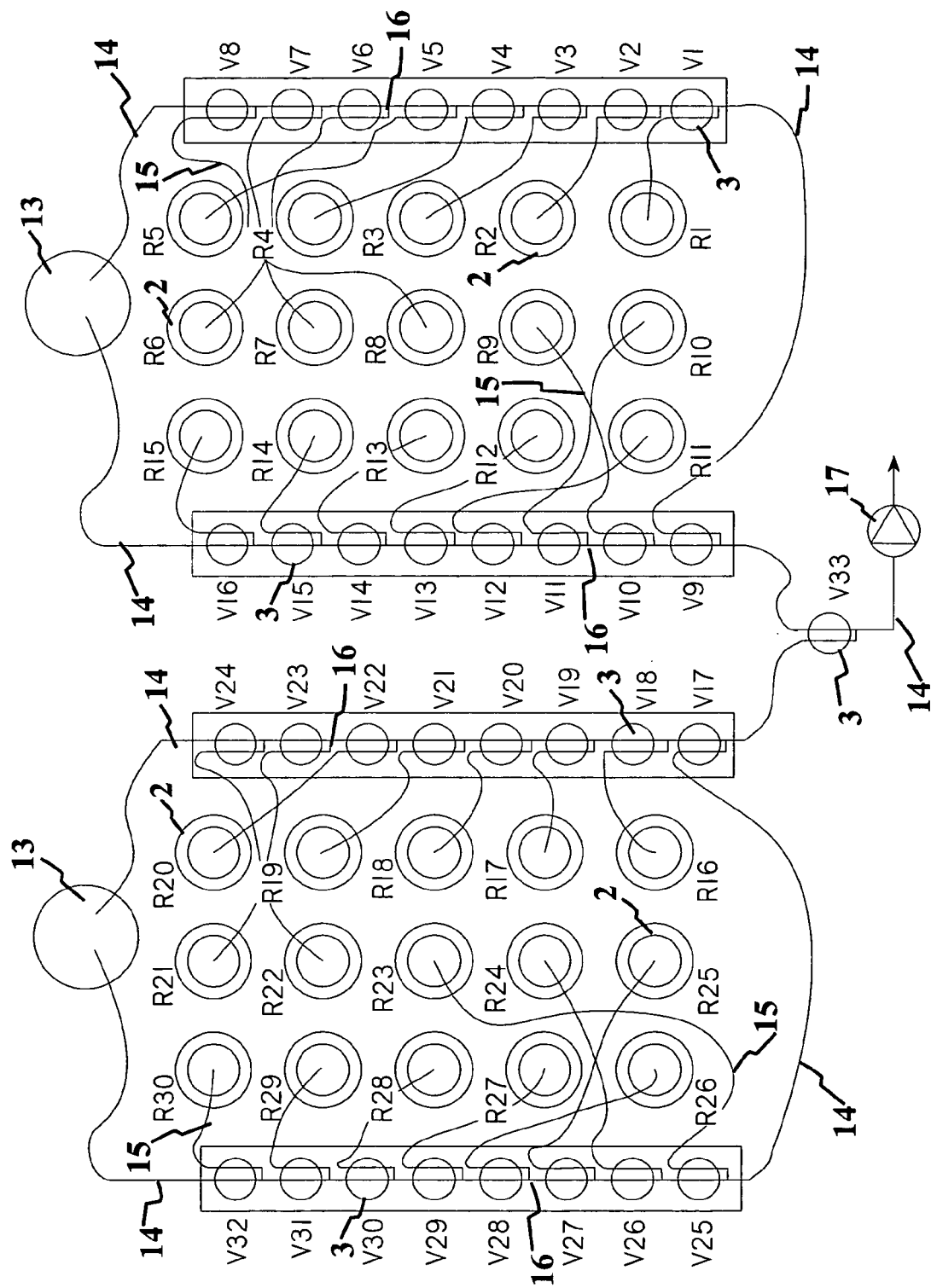
FIG. 5 shows a schematic presentation of the connections between the reactor vessels and the channel.
Figure 6:
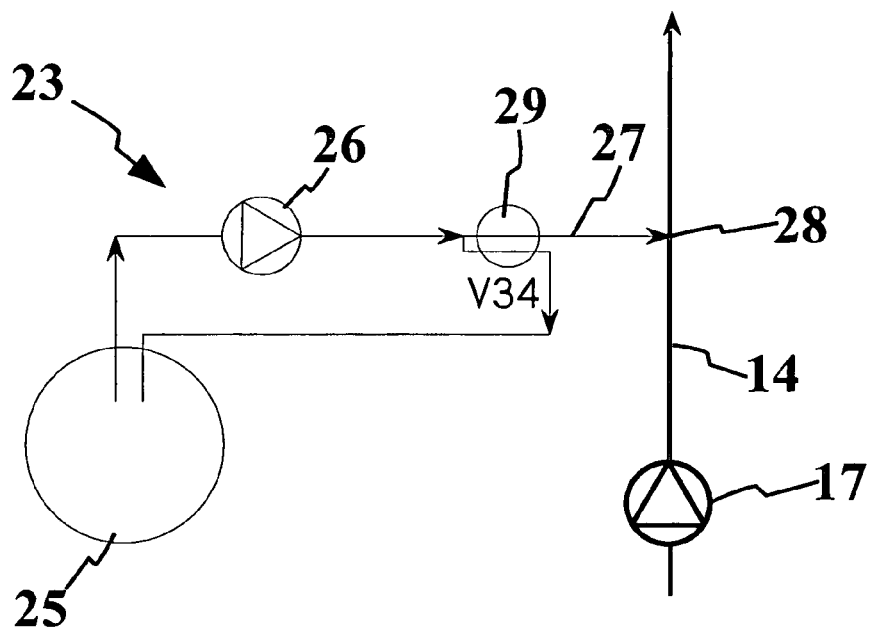
FIG. 6 shows a schematic presentation of a device delivering a chemical modification to the sample.
Figure 7:
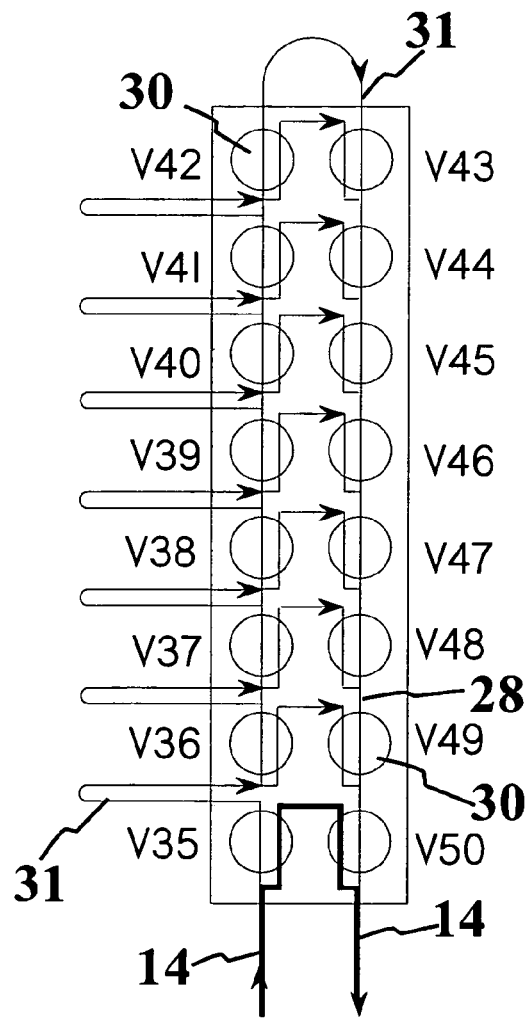
FIG. 7 shows a schematic presentation of a device controlling the contact time between the chemical modification fluid and the sample taken from the reactor device.

FIG. 5 shows a schematic presentation of the connections between the reactor vessels 2 and the channel 14. In FIG. 5 the channel 14 is branched into four branches, which are all connected to a source 13 of a cleaning fluid, such as to a container with 70%-ethanol. In FIG. 5 the source 13 of a cleaning fluid consists of two such containers. At the other end of the channel 14 a pump is arranged for delivering fluid from the channel 14 to the monitoring means. The pump 17 can be a peristaltic pump, for instance. Additionally, the channel 14 may also include a connection to a device 23 for delivering a chemical modification to the sample, as shown in FIG. 6. Furthermore, the channel 14 may include a device 24 for controlling the contact time between the chemical modification fluid and the sample, as shown in FIG. 7, before the chemically modified sample is further directed to the monitoring means (in-line device 4 and/or storage means 5).

FIG. 5 shows, by way of example, 30 reactor vessels 2 numbered from R1 to R30. Each reactor vessel 2 is connected by a flexible hose 15 to a connecting point 16 in the channel 14. The channel 14 consists preferably of flexible hoses to which the flexible hoses 15 from the reactor vessels are connected at the connecting points 16 by T-branches, for instance. Thus the flexible hoses and the T-branches can be removed and autoclaved before use.

The reactor device of FIG. 5 is provided with a valve 3 for each reactor vessel 2. In the case of FIG. 5 there are also additional valves, which make it possible to branch off the channel 14. The valves 3, which are numbered from V1 to V33 in FIG. 5, are illustrated as circles through which two flexible hoses (for instance 14 and 15) extend. Each valve has a pinching member (such as a part pressing against either hose in order to flatten it out) arranged, at each moment, to close one of these two flexible hoses (for instance 14 and 15) by pinching, while the other one of the two hoses (for instance 14 and 15) remains open. The advantage with such a solution is that the fluid pumped in the hoses does not at any stage come into contact with parts of the valve, but only with the hoses, which can be autoclaved.

In order to clean the channel 14 before taking a first sample from a reactor vessel, all valves 3 are set in a state where they close the hose 15 leading to the respective reactor vessel. Thus, when the pump starts, cleaning fluid will be delivered from the source 13 through the channel 14. In order to clean all of the branches of the channel 14, the state of the valves 3 marked with V9, V17 and V33 is changed while the delivery of the cleaning fluid is going on.

In order to take a sample from one of the reactor vessels 2, the state of the valves 3 marked with V1 to V33 is changed. For instance, in order to take a sample from the reactor vessel 2 marked with R14, the state of the corresponding valve 3 marked with V15 is changed. Thus the flexible hose 15 is opened and the channel 14 is closed up-streams in the channel as compared to the connection point 16 of the reactor vessel. At this stage the valve marked with V9 is in a state connecting the left branch, and valve marked with V33 is in a state connecting the right branch of the channel 14 to the pump 17. Thus fluid from the reactor vessel marked with R14 will enter the channel and be delivered to the monitoring means. When a sufficient volume has been obtained for a sample, the state of the valve 2 marked with V15 is changed again such that cleaning fluid can be delivered through the channel 14.

If necessary, the controller 7 of the reactor device can be programmed such that it controls the valves and the pump in such a way that the volume of the samples taken from different reactor vessels remains constant. In order to provide perturbation to the system it is also possible that the controller controls additional valves and/or pumps in order to feed new fluid to individual reactor vessels.

FIG. 6 shows a schematic presentation of a device 23, shown in FIG. 1 for delivering a chemical modification to the sample. Thus the device 23 can be connected to the channel 14 after the pump 17 in the embodiment of FIG. 5, for instance.

In order to chemically modify a sample taken from one of the reactor vessels 2, fluid from a container 25 aimed for chemical modification is pumped with a pump 26 through a flexible hose 27 simultaneously with the sample to a connector point 28 in the channel 14, where the sample and the fluid mix with each other. A pinching valve 29 marked with V34 is used to control whether the chemical modification fluid is actually pumped to the connection point or circulated back to the container 25. Thus, the contact between the chemical modification fluid and the sample is achieved by changing the state of valve V34. This valve 29 and the pump 26 can be controlled by the controller of the reactor device.

FIG. 7 shows a schematic presentation of a device 24 for controlling the contact time between a chemical modification fluid and a sample. The device 24, which has also been shown in FIG. 1, can be connected as an extension of the channel 14 after the connection point 28 shown in FIG. 6.

The device 24 consists of tubing and valves, which are mounted in a chamber whose temperature is kept within a predetermined temperature range. The chamber can also be overpressurized. The pinching valves 30 marked with V35 to V50 are illustrated as circles through which the flexible hose extend. The channel 14 is connected to two valves marked with V35 and V50. As presented in FIG. 7, the valves V35 to V50, and the hose 31 and channel 14 are arranged in such a way that the length of the flexible hose 31, through which the chemically modified sample is directed, can be altered by changing the state of the valves.

The length of the channel 14 is as short as possible when the valve V35 is in a state enabling flow to the right branch through the valve V50. If the valve V35 enables flow to the left branch, the flow enters the hose 31, which increases the length of the channel 14. If valve V36 simultaneously enables flow to the right branch to valve V49, the fluid travels the shortest length of the hose 31. The second shortest length of hose 31 is achieved if the valve V35 enables flow to the left branch to the hose 31; V36 enables flow to the left branch to valve V37; the valve 37 enables flow to right branch to valve V48; and valves V49 and V50 enable flow back to the channel 14. When using 16 valves, a maximum of 8 loops and also 8 different hose 31 lengths can be obtained. The contact time between the chemical modification fluid and the sample can be controlled by controlling the length of the hose 31 (and thus the length of the channel through which the chemically modified sample travels), the speed of the pump 17 (controlling the flow of the sample from reactor vessels 2), or the speed of the pump 26 (controlling the flow of the chemical modification fluid from container 25).

The overpressurized chamber, where the valves V35 to V50 are mounted in device 24, provides a possibility to create an atmosphere that is suitable for the chemical reactions occurring during the contact between the chemical modification fluid and the sample if a semi-permeable tubing is used in the device. For example, if the sample contains aerobic microbes, the chamber can be overpressurized with air. Furthermore, if silicone hose is used, oxygen from air diffuses through the hose to the sample. Thus, an oxygen limitation will not occur in the chemically modified sample during the contact between the chemical modification fluid and the sample.

Figure 8:
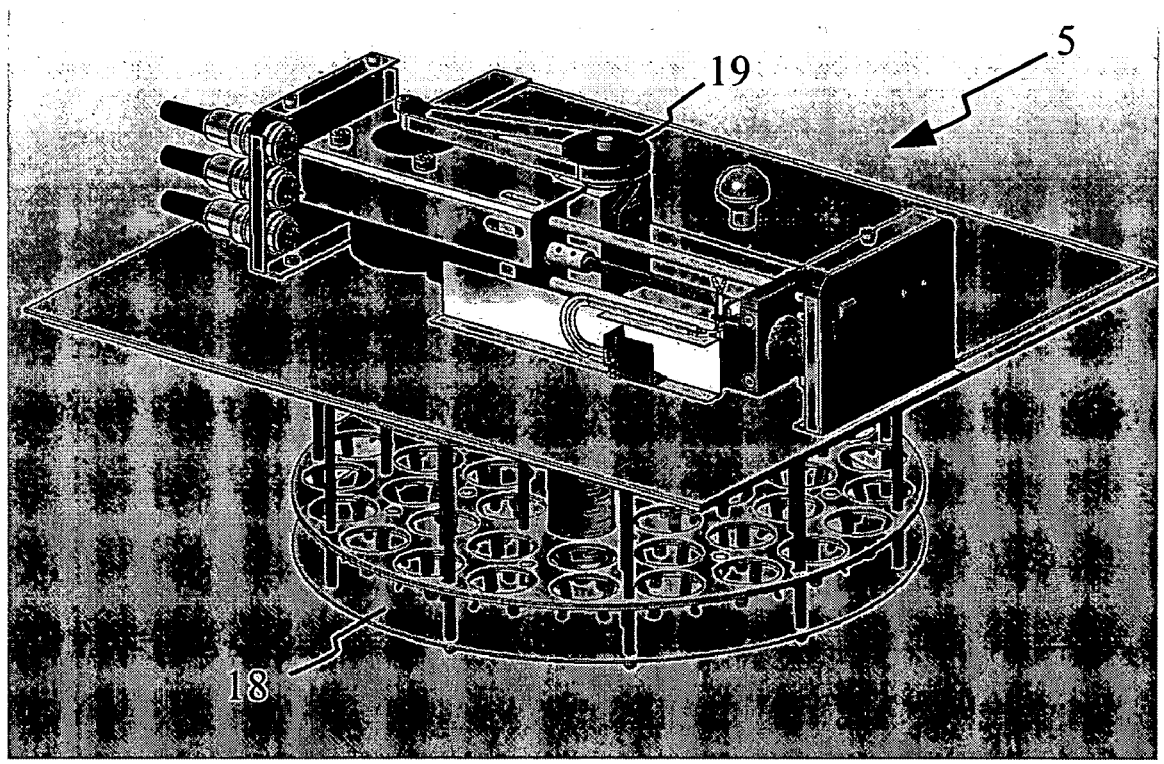
FIG. 8 shows details of a storage means.

FIG. 8 shows details of a storage means 5 shown in FIG. 1. The storage means 5 comprises a carousel 18 arranged to receive a plurality of containers. The containers can consist of glass bottles, for instance. The carousel 18 and the containers arranged in it are located during use in the cold chamber 6 described in connection with FIG. 1. The controller of the reactor device controls the operation of the storage device with actuators to move the containers and/or the channel such that samples taken from different reactor vessels are fed into different containers in the storage device 5. One such actuator is the stepping motor 19, which is used to rotate the carousel 18 of the storage device.

As is apparent from the description above, the reactor device is in a preferred embodiment capable of fully automatically taking samples from the microbial cultivations located in the reactor vessels, monitor cultivation parameters, and storing the samples separately for possible further actions. This minimizes the need for manual work and also, as the number of simultaneous cultivations can be large, increases the number of cultivations which can be handled during a specific period of time. The samples from different reactor vessels can be kept separate due to reactor-vessel-specific hoses 15 and valves 3. The common channel 14 used for pumping the samples can be cleaned automatically between each sample.

Figure 9:
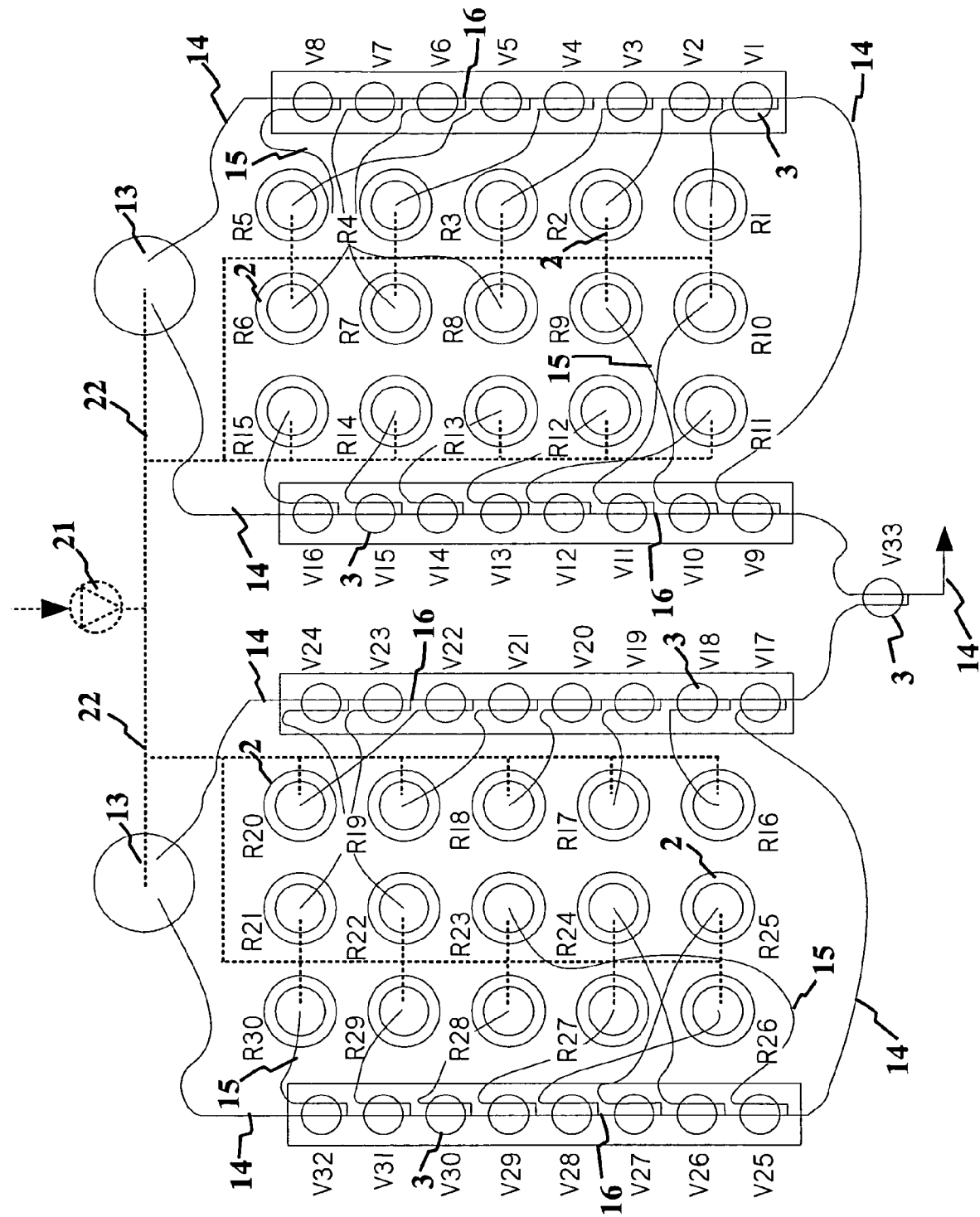
FIG. 9 shows a schematic presentation of a second preferred embodiment of the invention.

FIG. 9 shows a schematic presentation of a second preferred embodiment of the invention. FIG. 9 illustrates an embodiment that corresponds to the one described in connection with FIG. 5, except for the pump for delivering fluid to the monitoring means.

In FIG. 5 (and the other previously explained figures) it has been explained by way of example that a pump, such as a peristaltic pump, is used to deliver fluid from the reactor vessels 2 via the channel 14 to the monitoring means. In FIG. 9, however, no such pump is used. Instead the embodiment of FIG. 9 includes a compressor pump 21 and a pipeline 22.

The compressor pump 21 and the pipeline 22 are used to continuously deliver compressed air into the reactor vessels 2 and the source 13 for a cleaning fluid. Thus an overpressure is present in each reactor vessel and in the source for a cleaning fluid, which can consist of a closed container or of two such containers, as shown in FIG. 9. When one of the valves 3 is opened, then the overpressure in the corresponding reactor vessel 2 or cleaning fluid container will cause the fluid to be delivered to the monitoring means.

In addition to the compressor pump 21, the pipeline 22 can be connected to a container of compressed gas. Thus, overpressure can be applied in each reactor vessel 2 and in the source for cleaning fluid 13 by the means of a gas container.

It is to be understood that the above description and the accompanying figures are only intended to illustrate the present invention. It will be obvious to those skilled in the art that the invention can be varied and modified also in other ways without departing from the scope of the invention.

The invention claimed is:

1. A reactor device configured to handle microbial or unicellular liquid-phase cultivations, comprising:
   an inline device for obtaining measurement results from fluid samples,
   a storage for receiving a plurality of containers,
   a channel for delivering fluid samples to said inline device and said storage via said channel,
   reactor vessels for containing fluid, connected to said channel via valves, said reactor vessels comprising at least one inlet for introducing fluid into said reactor vessels via said inlets,
   a controller for controlling the fluid sample delivery, the inline device, the storage and the valves for taking fluid samples from selected reactor vessels one by one, and for delivering said fluid samples to the inline device and the storage via said channel,
   a source of a cleaning fluid which is connected to said channel via a valve, and said controller is configured to control said valve for cleaning said channel by delivering cleaning fluid through said channel, and
   an actuator for moving said plurality of containers received by said storage and/or an end of said channel such that fluid samples taken from the different reactor vessels are fed from the channel into different containers,
   wherein said controller is configured to control the reactor device for taking fluid samples from selected reactor vessels one by one, by controlling the reactor device to open a valve connecting a selected reactor vessel to said channel; to deliver a fluid sample from said selected reactor vessel to said inline device and said storage; to close said opened valve; to open said valve connecting the source of a cleaning fluid to said channel for delivering cleaning fluid through said channel between fluid samples taken from different reactor vessels; and to close said valve connecting the source of a cleaning fluid to said channel.

2. A reactor device configured to handle microbial or unicellular liquid-phase cultivations, comprising:
an inline device for obtaining measurement results from fluid samples,
a storage for receiving a plurality of containers,
a channel for delivering fluid samples to said inline device and said storage via said channel,
reactor vessels for containing fluid, connected to said channel via valves, said reactor vessels comprising at least one inlet for introducing fluid into said reactor vessels via said inlets,
a controller for controlling the fluid sample delivery, the inline device, the storage and the valves for taking fluid samples from selected reactor vessels one by one, and for delivering said fluid samples to the inline device and the storage via said channel,
a source of a cleaning fluid which is connected to said channel via a valve, and said controller is configured to control said valve for cleaning said channel by delivering cleaning fluid through said channel, and
an actuator for moving said plurality of containers received by said storage and/or an end of said channel such that fluid samples taken from the different reactor vessels are fed from the channel into different containers,
wherein said channel includes a flexible hose to which said reactor vessels are connected by flexible hoses at respective connecting points, and
wherein said reactor device includes for each reactor vessel a valve, which is responsive to control signals from said controller and arranged to close by pinching either the flexible hose connecting the respective reactor vessel to the channel or said flexible hose of the channel, at a point located up-stream in the channel as compared to the connection point of said reactor vessel, while the other one of said flexible hoses, which for the moment is not closed by pinching, remains open to allow a flow.

3. The reactor device of claim 1, wherein said reactor device comprises a device for delivering a second fluid, which is connected to said channel at a connector point, in order to mix said second fluid with a fluid sample in said channel.

4. The reactor device of claim 1, wherein said reactor device comprises a cold chamber, and that said containers received by the storage are located in said cold chamber.

5. The reactor device of claim 1, wherein said inline device includes one or more of the following: a device for measuring the pH of a fluid sample, a device for measuring the DO of a fluid sample, or a microscope with a camera for capturing a picture of a fluid sample.

6. A reactor device configured to handle microbial or unicellular liquid-phase cultivations, comprising:
an inline device for obtaining measurement results from fluid samples,
a storage for receiving a plurality of containers,
a channel for delivering fluid samples to said inline device and said storage via said channel,
reactor vessels for containing fluid, connected to said channel via valves, said reactor vessels comprising at least one inlet for introducing fluid into said reactor vessels via said inlets,
a controller for controlling the fluid sample delivery, the inline device, the storage and the valves for taking fluid samples from selected reactor vessels one by one, and for delivering said fluid samples to the inline device and the storage via said channel,
a source of a cleaning fluid which is connected to said channel via a valve, and said controller is configured to control said valve for cleaning said channel by delivering cleaning fluid through said channel, and
an actuator for moving said plurality of containers received by said storage and/or an end of said channel such that fluid samples taken from the different reactor vessels are fed from the channel into different containers,
wherein the controller is configured to control said valves and said fluid sample delivery such that the volume of fluid samples taken from different reactor vessels is substantially constant.

7. The reactor device of claim 1, wherein said reactor device comprises a fluid bath arranged to adjust the temperature of the fluid bath, wherein said reactor vessels are arranged.

8. A reactor device configured to handle microbial or unicellular liquid-phase cultivations, comprising:
an inline device for obtaining measurement results from fluid samples,
a storage for receiving a plurality of containers,
a channel for delivering fluid samples to said inline device and said storage via said channel,
reactor vessels for containing fluid, connected to said channel via valves, said reactor vessels comprising at least one inlet for introducing fluid into said reactor vessels via said inlets,
a controller for controlling the fluid sample delivery, the inline device, the storage and the valves for taking fluid samples from selected reactor vessels one by one, and for delivering said fluid samples to the inline device and the storage via said channel,
a source of a cleaning fluid which is connected to said channel via a valve, and said controller is configured to control said valve for cleaning said channel by delivering cleaning fluid through said channel, and
an actuator for moving said plurality of containers received by said storage and/or an end of said channel such that fluid samples taken from the different reactor vessels are fed from the channel into different containers,
wherein said reactor device comprises additional valves arranged in said channel to direct fluid samples passing through said channel to flow via alternative fluid paths of mutually different length in order to adjust the time needed for delivering a fluid sample through said channel.

* * * * *

UNITED STATES PATENT AND TRADEMARK OFFICE
CERTIFICATE OF CORRECTION

PATENT NO. : 7,632,673 B2  Page 1 of 1
APPLICATION NO. : 11/261604
DATED : December 15, 2009
INVENTOR(S) : Juha-Pekka Pitkanen et al.

It is certified that error appears in the above-identified patent and that said Letters Patent is hereby corrected as shown below:

On the Title page, Item (75), please correct inventor Antti Vuolanto's given name as follows:

Delete "Antii" and insert --Antti--.

Signed and Sealed this

Sixteenth Day of March, 2010

David J. Kappos
*Director of the United States Patent and Trademark Office*